United States Patent [19]

Reiffenrath et al.

[11] Patent Number: 5,055,223
[45] Date of Patent: Oct. 8, 1991

[54] ARYL-SULFUR PENTAFLUORIDES

[75] Inventors: Volker Reiffenrath, Rossforf; Rudolf Eidenschink, Bodenheim; Georg Weber, Erzhausen, all of Fed. Rep. of Germany

[73] Assignee: Merck Patent Gesellschaft Mit Beschrankter Haftung, Darmstadt, Fed. Rep. of Germany

[21] Appl. No.: 455,357

[22] PCT Filed: Jun. 14, 1988

[86] PCT No.: PCT/EP88/00530

§ 371 Date: Dec. 27, 1989

§ 102(e) Date: Dec. 27, 1989

[87] PCT Pub. No.: WO88/10251

PCT Pub. Date: Dec. 29, 1988

[30] Foreign Application Priority Data

Jun. 27, 1987 [DE] Fed. Rep. of Germany ....... 3721268

[51] Int. Cl.$^5$ .............. C09K 19/32; C09K 19/34; C09K 19/20; G02F 1/13
[52] U.S. Cl. ............ 252/299.62; 252/299.61; 252/299.63; 252/299.66; 252/299.67; 252/299.68; 359/103; 560/64; 560/100; 568/74; 568/77; 544/298; 558/412; 558/289; 558/272
[58] Field of Search ...... 252/299.62, 299.68, 252/299.67, 299.63; 350/350 R; 560/64, 100, 299.61; 568/74, 77; 544/298; 558/412, 289, 272

[56] References Cited

U.S. PATENT DOCUMENTS

| 3,102,903 | 9/1963 | Coffman et al. ............ 568/74 X |
| 4,481,149 | 11/1984 | Misaki et al. ............ 558/416 X |
| 4,696,759 | 9/1987 | Isoyama et al. ............ 252/299.62 |
| 4,871,469 | 10/1989 | Reiffenrath et al. ......... 252/299.61 |

FOREIGN PATENT DOCUMENTS

| 0149209 | 7/1985 | European Pat. Off. ........ 350/350 R |
| 2916358 | 11/1980 | Fed. Rep. of Germany ....... 560/64 |

Primary Examiner—Robert L. Stoll
Assistant Examiner—Cynthia Harris
Attorney, Agent, or Firm—Millen, White & Zalano

[57] ABSTRACT

Aryl-sulfur pentafluorides of the formula I

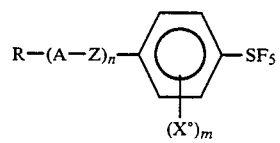

wherein R, A, Z, n, m and X° have the meaning indicated in claim 1 are suitable for use as components of liquid-crystal phases for field-effect and/or bi-stability effect displays.

4 Claims, No Drawings

ARYL-SULFUR PENTAFLUORIDES

The invention relates to new aryl-sulfur pentafluorides of the formula I

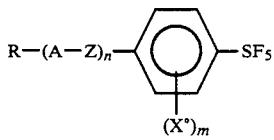

wherein

R is H, Y or an alkyl or alkenyl radical each of which has 1-15 C atoms and is unsubstituted or substituted by at least one group Y and in which one or more non-adjacent $CH_2$ groups can also be replaced by O and/or S atoms and/or by —E—, —CO—, —O—CO—, —CO—O—, —O—CO—O—, —S—CO— and/or —CO—S— groups, E is C≡C,

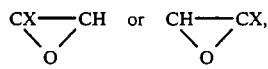

the $X^o$s independently of one another are each Y or $CH_3$, the Xs independently of one another are each $X^o$ or H, Y is CN, $N_3$, NCO, NCS, fluorine or chlorine, the As independently of one another are each a) a 1,4-cyclohexylene radical, wherein one or two non-adjacent $CH_2$ groups can be replaced by O atoms, b) a 1,4-phenylene radical, wherein one or more CH groups can be replaced by N, or c) a radical belonging to the group comprising 1,4-cyclohexenylene, piperidine-1,4-diyl, bicyclo-(2.2.2)octylene, naphthalene-2,6-diyl, decahydronaphthalene-2,6-diyl or 1,2,3,4-tetrahydronaphthalene, it being possible for the radicals a) and b) to be monosubstituted or disubstituted by $X^o$, the Zs independently of one another are each —CO—O—, —O—CO—, —CH₂CH₂—, —CHCN—CH₂—, —CH₂—CHCN—, —CH=CH—, —C≡C—, —OCH₂—, —CH₂O—, —CH=N—, —N=CH—, —NO=N—, —N=NO— or a single bond, m is 0, 1 or 2 and n is 1, 2 or 3.

For the sake of simplicity, in what follows Phe is a 1,4-phenylene group, Cy is a trans-1,4-cyclohexylene group, Che is a cyclohexenylene group, Bi is a bicyclo-(2.2.2)octylene group, Pyd is a pyridine-2,5-diyl group, Pyr is a pyrimidine-2,5-diyl group, Pip is a piperidine-1,4-diyl group, Dit is a 1,3-dithiane-2,5-diyl group and Dio is a 1,3-dioxane-2,5-diyl group, it being possible for these groups to be unsubstituted or substituted.

Phe X is a group of the formula

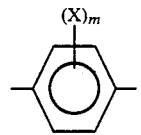

in which X in what follows is preferably chlorine or fluorine.

The compounds of the formula I can, like similar compounds, be used as a component of liquid-crystal phases, in particular for displays based on the principle of the twisted cell, the guest-host effect, the effect of the deformation of aligned phases, the effect of dynamic scattering or the 2-frequency method.

The compounds of the formula I are also suitable for use as components of phases for use in SBE, STN or OMI displays.

The invention was based on the task of indicating a stable liquid-crystal or mesogenic compound suitable for use as a component of liquid-crystal phases.

It has been found that the aryl-sulfur pentafluorides of the formula I are excellently suitable for use as components of liquid-crystal phases. In particular, they have comparatively low viscosities and exhibit no tendency, or only a slight tendency, to form molecular associates, while, at the same time, having a pronounced positive dielectric anisotropy. It is possible with their aid to obtain stable liquid-crystal phases having a broad mesophase range, advantageous values for optical and dielectric anisotropy and favourable elastic properties.

In addition, the provision of compounds of the formula I widens considerably, in a very general manner, the range of liquid-crystal substances suitable from various aspects of technical performance for the preparation of liquid-crystal mixtures.

The compounds of the formula I possess a wide field of use. Depending on the selection of the substituents, these compounds can be used as the base materials of which liquid-crystal phases are predominantly composed; it is also possible, however, to add compounds of the formula I to liquid-crystal base materials composed of other classes of compounds in order, for example, to influence the dielectric and/or optical anisotropy of such a dielectric and/or to reduce the threshold voltage and or viscosity thereof.

In the pure state, the compounds of the formula I are colourless and they form liquid-crystal mesophases within a temperature range which is advantageously situated for electrooptical use. They are stable to chemicals, heat and light.

The invention thus relates to the aryl-sulfur pentafluorides of the formula I and to a process for their preparation which is characterized in that p-lithiumaryl- or bromomagnesium-aryl-sulfur pentafluorides are reacted with appropriate electrophiles, or corresponding 1-alkynes are coupled with p-bromoaryl-sulfur pentafluorides with transition metal catalysis, or a compound which otherwise corresponds to the formula I, but contains one or more reducible groups and/or C—C bonds instead of H atoms, is treated with a reducing agent, or, in order to prepare esters of the formula I (wherein Z is —CO—O— or —O—CO— and/or R contains a carboxyl group), a corresponding carboxylic acid or one of its reactive derivatives is reacted with a corresponding alcohol or one of its reactive derivatives, or, in order to prepare ethers of the formula I (wherein R is an alkoxy group and/or Z is an —OCH$_2$— or —CH$_2$O— group), a corresponding hyroxy compound is etherified.

The invention also relates to the use of the compounds of the formula I as components of liquid-crystal phases. The invention also relates to liquid-crystal phases containing at least one compound of the formula I and also to liquid-crystal display elements, in particular electrooptical display elements, containing phases of this type.

The compounds of the formula I accordingly embrace compounds of the partial formulae Ia to Id (having two rings).

| | |
|---|---|
| R—A—Phe—SF$_5$ | Ia |
| R—A—PheX—SF$_5$ | Ib |
| R—A—Z—Phe—SF$_5$ | Ic |
| R—A—Z—PheX—SF$_5$ | Id |
| Ie to Il (having 3 rings) | |
| R—A—A—Phe—SF$_5$ | Ie |
| R—A—A—PheX—SF$_5$ | If |
| R—A—A—Z—Phe—SF$_5$ | Ig |
| R—A—A—Z—PheX—SF$_5$ | Ih |
| R—A—Z—A—Phe—SF$_5$ | Ii |
| R—A—Z—A—PheX—SF$_5$ | Ij |
| R—A—Z—A—Z—Phe—SF$_5$ | Ik |
| R—A—Z—A—Z—PheX—SF$_5$ | Il |
| and Im to Izb (having 4 rings) | |
| R—A—A—A—Phe—SF$_5$ | Im |
| R—A—A—A—PheX—SF$_5$ | In |
| R—A—A—A—Z—Phe—SF$_5$ | Io |
| R—A—A—A—Z—PheX—SF$_5$ | Ip |
| R—A—A—Z—A—Phe—SF$_5$ | Iq |
| R—A—A—Z—A—PheX—SF$_5$ | Ir |
| R—A—Z—A—A—Phe—SF$_5$ | Is |
| R—A—Z—A—A—PheX—SF$_5$ | It |
| R—A—A—Z—A—Z—Phe—SF$_5$ | Iu |
| R—A—A—Z—A—Z—PheX—SF$_5$ | Iv |
| R—A—Z—A—A—Z—Phe—SF$_5$ | Iw |
| R—A—Z—A—A—Z—PheX—SF$_5$ | Ix |
| R—A—Z—A—Z—A—Phe—SF$_5$ | Iy |
| R—A—Z—A—Z—A—PheX—SF$_5$ | Iz |
| R—A—Z—A—Z—A—Z—Phe—SF$_5$ | Iza |
| R—A—Z—A—Z—A—Z—Phe—SF$_5$ | Izb |

Amongst these, the compounds of the partal formulae Ia, Id, Ie and Ig are particularly preferred.

In the compounds of the preceding and following formulae, R is preferably alkyl, and also alkoxy. Further preferred meanings are oxaalkyl, in particular 2-oxaalkyl, and alkenyl.

The groups A, which can be identical or different, are preferably Cy, Phe, PheX, Pyd or Pyr; Cy or Phe are particularly preferred; preferably, the compounds of the formula I do not contain more than one of the radicals Bi, Pyd or Pyr.

In the preceding and following compounds of the formula I and all partial formulae of I, PheX is preferably a 1,4-phenylene group, which is monosubstituted or disubstituted by fluorine or chlorine atoms or by methyl or cyano groups. 2-Fluoro-1,4-phenylene, 3-fluoro-1,4-phenylene and 2,3-difluoro-1,4-phenylene groups are particularly preferred.

n is preferably 1 or 2, particularly preferably 1.

The groups Z, which can be identical or different, are preferably single bonds and, as a second preference, —CO—O—, —O—CO—, —C≡C— or —CH$_2$CH$_2$— groups. Compounds of the formula I wherein all the groups Z are single bonds or one group Z (preferably the group Z attached to PheX-SF$_5$) is —CO—O—, —O—CO— or —CH$_2$CH$_2$— are particularly preferred.

If R is an alkyl radical and/or an alkoxy radical, this can be linear or branched. Preferably, it is linear, has 2, 3, 4, 5, 6 or 7 C atoms and accordingly is preferably ethyl,propyl, butyl, pentyl, hexyl, heptyl, ethoxy, propoxy, butoxy, pentoxy, hexoxy or heptoxy, and also methyl, octyl, nonyl, decyl, undecyl, dodecyl, tridecyl, tetradecyl, pentadecyl, methoxy, octyloxy, nonyloxy, decyloxy, undecyloxy, dodecyloxy, tridecyloxy or tetradecyloxy.

Oxaalkyl is preferably linear 2-oxapropyl (=methoxymethyl), 2-oxabutyl (=ethoxymethyl) or 3-oxabutyl (=2-methoxyethyl), 2-, 3- or 4-oxapentyl, 2-, 3-, 4- or 5-oxahexyl, 2-, 3-, 4-, 5- or 6-oxaheptyl, 2-, 3-, 4-, 5-, 6- or 7-oxaoctyl, 2-, 3-, 4-, 5-, 6-, 7- or 8-oxanonyl or 2-, 3-, 4-, 5-, 6-, 7-, 8- or 9-oxadecyl.

If R is an alkenyl radical, it can be linear or branched. It is preferably linear and has 2 to 10 C atoms. Accordingly, it is particularly vinyl, prop-1-enyl, prop-2-enyl, but-1-, but-2- or but-3-enyl, pent-1-, -2-, -3- or -4-enyl, hex-1-, -2-, -3-, -4- or -5-enyl, hept-1-, -2-, -3-, -4-, -5- or -6-enyl, oct-1-, -2-, -3-, -4-, -5-, -6- or -7-enyl, non-1-, -2-, -3-, -4-, -5-, -6-, -7- or -8-enyl or dec-1-, -2-, -3-, -4-, -5-, -6-, -7-, -8- or -9-enyl.

If R is an alkyl radical in which a CH$_2$ group has been replaced by —O—CO— or —CO—O—, it is preferably linear and has 2 to 6 C atoms. Accordingly it is particularly acetoxy, propionyloxy, butyryloxy, pentanoyloxy, hexanoyloxy, acetoxymethyl, propionyloxymethyl, butyryloxymethyl, pentanoyloxymethyl, 2-acetoxyethyl, 2-propionyloxyethyl, 2-butyryloxyethyl, 3-acetoxypropyl, 3-propionyloxypropyl, 4-acetoxybutyl, methoxycarbonyl, ethoxycarbonyl, propoxycarbonyl, butoxycarbonyl, pentoxycarbonyl, methoxycarbonylmethyl, ethoxycarbonylmethyl, propoxycarbonylmethyl, butoxycarbonylmethyl, 2-(methoxycarbonyl)ethyl, 2-(ethoxycarbonyl)ethyl, 2-(propoxycarbonyl)ethyl, 3-(methoxycarbonyl)propyl, 3-(ethoxycarbonyl)propyl or 4-(methoxycarbonyl)-butyl.

If R is an alkenyl radical in which a CH$_2$ group adjacent to the C=C double bond has been replaced by —CO— or —CO—O— or —O—CO—, it can be linear or branched. It is preferably linear and has 4 to 13 C atoms. Accordingly it is particularly acryloyloxymethyl, 2-acryloyl-oxyethyl, 3-acryloyloxypropyl, 4-atryloyloxybutyl, 5-acryloyloxypentyl, 6-acryloyloxyhexyl, 7-acryloyloxyheptyl, 8-acryloyloxyoctyl, 9-acryloyloxynonyl, 10-acryloyloxydecyl, methacryloyloxymethyl, 2-methacryloyloxyethyl, 3-methacryloyloxypropyl, 4-methacryloyloxybutyl, 5-methacryloyloxypentyl, 6-methacryloyloxyhexyl, 7-methacryloyloxyheptyl, 8-methacryloyloxyoctyl or 9-methacryloyloxynonyl.

Compounds of the formula I having wing groups R which are suitable for polymerization reactions are suitable for the preparation of liquid-crystal polymers.

Ccmpounds of the formulae I having branched wing groups R can, occasionally, be of importance owing to improved solubility in the customary liquid-crystal base materials, but are of particular importance as chiral doping agents, if they are optically active. Smectic compounds of this type are suitable for use as components of ferroelectric materials.

As a rule, branched groups of this type do not contain more than one chain branching. Preferred branched radicals R are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-propylpentyl, isopropoxy, 2-methylpropoxy, 2-methylbutoxy, 3-methylbutoxy, 2-methylpentoxy, 3methylpentoxy, 2-ethylhexoxy, 1-methylhexoxy and 1methylheptoxy.

If R is an alkyl radical in which two or more CH$_2$ groups have been replaced by —O— and/or —CO—O—, it can be linear or branched. It is preferably branched and has 3 to 12 C atoms. Accordingly it is particularly bis-(carboxy)-methyl, 2,2-bis-(carboxy)-ethyl, 3,3-bis-(carboxy)-propyl, 4,4-bis-(carboxy)-butyl, 5,5-bis-(carboxy)-pentyl, 6,6-bis-(carboxy)-hexyl, 7,7-bis-(carboxy)-heptyl, 8,8-bis-(carboxy)-octyl, 9,9-bis-(carboxy)-nonyl, 10,10-bis-(carboxy)-decyl, bis-(methoxy-carbonyl)-methyl, 2,2-bis-(methoxycarbonyl)-ethyl, 3,3-bis-(methoxycarbonyl)-propyl, 4,4-bis-(methoxycarbonyl)-butyl, 5,5-bis-(methoxycarbonyl)-pentyl, 6,6-bis-(methoxy-carbonyl)-hexyl, 7,7-bis-(methoxycarbonyl)-heptyl, 8,8-bis-(methoxycarbonyl)-octyl, bis-(ethoxycarbonyl)-methyl, 2,2-bis-(ethoxycarbonyl)-ethyl, 3,3-bis-(ethoxycarbonyl)-propyl, 4,4-bis-(ethoxycarbonyl)-butyl or 5,5-bis-(ethoxy-carbonyl)-pentyl.

Compounds of the formula I having wing groups R which are suitable for polycondensation reactions are suitable for the preparation of liquid-crystal polycondensates.

Formula I embraces both the racemates of these compounds and the optical antipodes and mixtures thereof.

If the compounds of the formula I contain an asymmetric C atom, the formula I embraces racemates and also optically active enantiomers and mixtures of enantiomers.

Amongst the compounds of the formula I and all the preceding and following partial formulae of I, preferred compounds are those in which at least one of the radicals present therein has one of the preferred meanings indicated.

Accordingly, preferred compounds of the partial formula Ia include those of the partial formulae Iaa to Iaj:

| R—Phe—Phe—SF$_5$ | Iaa |
| R—PheX—Phe—SF$_5$ | Iab |
| R—Cy—Phe—SF$_5$ | Iac |
| R—Che—Phe—SF$_5$ | Iad |
| R—Bi—Phe—SF$_5$ | Iae |
| R—Pyd—Phe—SF$_5$ | Iaf |
| R—Pip—Phe—SF$_5$ | Iag |
| R—Dio—Phe—SF$_5$ | Iah |
| R—Dit—Phe—SF$_5$ | Iai |
| R—Pyr—Phe—SF$_5$ | Iaj |

Amongst the compounds of the partial formulae IbII, particular preference attaches to those of the partial formulae I1 to I48:

| R—Phe—PheX—SF$_5$ | I1 |
| R—Cy—PheX—SF$_5$ | I2 |
| R—Bi—PheX—SF$_5$ | I3 |
| R—Pyr—PheX—SF$_5$ | I4 |
| R—Pyd—PheX—SF$_5$ | I5 |
| R—Phe—COO—Phe—SF$_5$ | I6 |
| R—Cy—COO—Phe—SF$_5$ | I7 |
| R—Bi—COO—Phe—SF$_5$ | I8 |
| R—Phe—COO—PheX—SF$_5$ | I9 |
| R—Cy—COO—PheX—SF$_5$ | I10 |
| R—Bi—COO—PheX—SF$_5$ | I11 |
| R—Phe—C≡C—Phe—SF$_5$ | I12 |
| R—Cy—C≡C—Phe—SF$_5$ | I13 |
| R—Cy—C≡C—PheX—SF$_5$ | I14 |
| R—Phe—C≡C—PheX—SF$_5$ | I15 |
| R—Bi—CH$_2$CH$_2$—Phe—SF$_5$ | I16 |
| R—Cy—CH$_2$CH$_2$—PheX—SF$_5$ | I17 |
| R—Bi—CH$_2$CH$_2$—PheX—SF$_5$ | I18 |
| R—PheX—COO—Phe—SF$_5$ | I19 |
| R—Dio—PheX—SF$_5$ | I20 |
| R—Cy—CH$_2$CH$_2$—Phe—SF$_5$ | I21 |
| R—Cy—CH$_2$—O—Phe—SF$_5$ | I22 |
| R—Cy—Cy—Phe—SF$_5$ | I23 |
| R—Cy—Cy—PheX—SF$_5$ | I24 |
| R—Cy—Bi—Phe—SF$_5$ | I25 |
| R—Cy—Che—Phe—SF$_5$ | I26 |
| R—Dio—Cy—Phe—SF$_5$ | I27 |
| R—Cy—Phe—Phe—SF$_5$ | I28 |
| R—Cy—Phe—PheX—SF$_5$ | I29 |
| R—Phe—Phe—Phe—SF$_5$ | I30 |
| R—Phe—Phe—PheX—SF$_5$ | I31 |
| R—Cy—Cy—CO$_2$—Phe—SF$_5$ | I32 |
| R—Dit—Cy—Phe—SF$_5$ | I33 |
| R—Cy—Cy—CO$_2$—PheX—SF$_5$ | I34 |
| R—Bi—Phe—OCO—Phe—SF$_5$ | I35 |
| R—Cy—Phe—CO$_2$—PheX—SF$_5$ | I36 |
| R—Dio—Phe—CO$_2$—PheX—SF$_5$ | I37 |
| R—Cy—Phe—CO$_2$—Phe—SF$_5$ | I38 |
| R—Dit—Phe—CO$_2$—Phe—SF$_5$ | I39 |
| R—Cy—Phe—O—CO—Phe—SF$_5$ | I40 |
| R—Pym—Phe—O—CO—Phe—SF$_5$ | I41 |
| R—Cy—Phe—C≡C—Phe—SF$_5$ | I42 |
| R—Cy—Phe—CH$_2$CH$_2$—Phe—SF$_5$ | I43 |
| R—Py—Phe—C≡C—Phe—SF$_5$ | I44 |
| R—Dio—Phe—C≡C—Phe—SF$_5$ | I45 |
| R—Phe—Che—Phe—SF$_5$ | I46 |
| R—Cy—Che—PheX—SF$_5$ | I47 |
| R—Bi—Che—Phe—SF$_5$ | I48 |

Preferred compounds of the partial formulae Im to Izb are those of the partial formulae I49 to I59:

| R—Cy—Phe—Cy—Phe—SF$_5$ | I49 |
| R—Cy—Cy—Phe—Phe—SF$_5$ | I50 |
| R—Cy—PheX—Phe—COO—Phe—SF$_5$ | I51 |
| R—Cy—Phe—Phe—Phe—SF$_5$ | I52 |
| R—Cy—Phe—Phe—C≡C—Phe—SF$_5$ | I53 |
| R—Phe—Phe—Cy—CO$_2$—Phe—SF$_5$ | I54 |
| R—Phe—Phe—Che—CO$_2$—Phe—SF$_5$ | I55 |
| R—Phe—Phe—OCO—Che—Phe—SF$_5$ | I56 |
| R—Phe—Phe—OCO—Cy—Phe—SF$_5$ | I57 |
| R—Cy—Phe—Phe—O—CO—Phe—SF$_5$ | I58 |
| R—Cy—Phe—Phe—O—CH$_2$—Phe—SF$_5$ | I59 |

The compounds of the formula I are prepared bny methods known per se, such as are described in the literature (for example in the standard works such as Houben Weyl, Methoden der Organischen Chemie "Methods of Organic Chemistry" Georg-Thieme-Verlag, Stuttgart) from 4-substituted phenyl-sulfur pentafluorides, which are obtained, for example, in accordance with the literature (W. A. Sheppard, J. Am. Chem. Soc. 84, 3064, 1962).

The starting material here is di-(p-nitrophenyl) disulfide, which when reacted with silver difluoride, gives p-nitrophenyl-sulfur pentafluoride, which, in turn, can be used as the starting compound for many 4-substituted phenyl-sulfur pentafluorides.

The starting materials can, if desired, also be formed in situ, by a process in which they are not isolated from the reaction mixture, but are immediately reacted further to give the compounds of the formula I.

Esters of the formula I (R=alkyl wherein one or two CH$_2$ groups have been replaced by —O—CO— and/or —CO—O— groups and/or Z is —CO—O— or —O—CO—) can also be obtained by esterifying corresponding carboxylic acids (or their reactive derivatives) with alcohols or phenols (or their reactive derivatives).

Suitable reactive derivatives of the carboxylic acids mentioned are, in particular, the acid halides, above all the chlorides and bromides, and also the anhydrides, azides or esters, in particular alkyl esters having 1-4 C atoms in the alkyl group.

Suitable reactive derivatives of the alcohols or phenols mentioned are, in particular, the corresponding metal alcoholates or phenates, respectively, preferably of an alkali metal, such as Na or K. The esterification is advantageously carried out in the presence of an inert solvent. Suitable solvents are, in particular, ethers, such as diethyl ether, di-n-butyl ether, THF, dioxane or anisole, ketones, such as acetone, butanone or cyclohexanone, amides, such as DMF, N,N-dimethylpropyleneurea or phosphoric acid hexamethyltriamide, hydrocarbons, such as benzene, toluene or xylene, halogenated hydrocarbons, such as methylene dichloride, carbon tetrachloride or tetrachloroethylene, and sulfoxides, such as dimethyl sulfoxide or sulfolan. Water-immiscible solvents can, at the same time, be used advantageously in order to remove by azeotropic distillation the water formed in the course of the esterification. Occasionally, an excess of an organic base, for example pyridine, quinoline or triethylamine, can also be used as the solvent for the esterification. The esterification can also be carried out in the absence of a solvent, for example merely by heating the components in the presence of sodium acetate. The reaction temperature is usually between $-50°$ and $+250°$, preferably between $-20°$ and $+80°$. At these temperatures the esterification reactions are, as a rule, complete after 15 minutes to 48 hours.

In an individual case the reaction conditions for the esterification depend largely on the nature of the starting materials used. Thus a free carboxylic acid will, as a rule, be reacted with a free alcohol or phenol in the presence of a strong acid, for example a mineral acid such as hydrochloric acid or sulfuric acid. A preferred mode of reaction is the reaction of an acid anhydride, or especially an acid chloride, with an alcohol, preferably in a basic medium, and bases of importance are, in particular, alkali metal hydroxides, such as sodium hydroxide or potassium hydroxide, alkali metal carbonates or bicarbonates, such as sodium carbonate, sodium bicarbonate, potassium carbonate or potassium bicarbonate, alkali metal acetates, such as sodium acetate or potassium acetate, alkaline earth metal hydroxides, such as calcium hydroxide, or organic bases, such as triethylamine, pyridine, lutidine, collidine or quinoline. A further preferred embodiment of the esterification consists in first converting the alcohol or the phenol into the sodium or potassium alcoholate or phenate, respectively, for example by treatment with ethanolic sodium hydroxide or potassium hydroxide solution, isolating this alcoholate or phenate and reacting it with an acid anhydride or, in particular, an acid chloride.

A preferred embodiment of the esterification for the preparation of the esters of the formula I is the reaction of the corresponding carboxylic acid with the corresponding alcohol or phenol under the dehydrating action of carbodiimides, in particular dicyclohexylcarbodiimide, in an inert solvent, if appropriate with the use of 4-N,N-dimethylaminopyridine as a catalyst to accelerate the reaction.

Ethers of the formula I (wherein R is an alkyl group in which one or two $CH_2$ groups have been replaced by 0 atoms, and/or wherein $Z^1$ and/or $Z^2$ is an $-OCH_2-$ group or a $-CH_2O-$ group) can be obtained by etherifying corresponding phenols, the hydroxy compound being preferably first converted into a corresponding metal derivative, for example into the corresponding alkali metal alcoholate or alkali metal phenate by treatment with NaH, $NaNH_2$, NaOH, KOH, $Na_2CO_3$ or $K_2CO_3$. This alcoholate or phenate can then be reacted with the corresponding alkyl halide or sulfonate or dialkyl sulfonate, preferably in an inert solvent, such as acetone, 1,2-dimethoxyethane, DMF or dimethyl sulfoxide, or an excess of aqueous or aqueous-alcoholic NaOH or KOH, at temperatures between 20° and 100°.

In order to prepare fluorine or chlorine compounds of the formula I (wherein A is an aromatic structure and R has the customary meaning) which are substituted in the side chain, corresponding aniline derivatives can be reacted with sodium nitrite and converted, either by means of tetrafluoboric acid (in order to introduce an F atom) or by means of copper-(I) chloride (in order to introduce a Cl atom), to give the diazonium salts, which are then decomposed by heat at temperatures of 100°-140°.

The attachment of an aromatic nucleus to a non-aromatic nucleus or to two non-aromatic nuclei is preferably obtained by subjecting an organolithium or organomagnesium compound to a condensation reaction with a ketone or an aldehyde or ketone, if an aliphatic group Z is intended to be between the nuclei.

The organometallic compounds are prepared, for example, by metal-halogen exchange (for example as in Org. React. 6, 339-366 (1951)) between the corresponding halogen compound and an organolithium compound, such as, preferably, tert.-butyllithium or lithium naphthalide, or by reaction with magnesium turnings.

The attachment of two aromatic rings or one aliphatic group Z to an aromatic ring is preferably effected by Friedel-Crafts alkylation or acylation by reacting the corresponding halogen compounds with the corresponding aromatic compound with catalysis by a Lewis acid. Examples of suitable Lewis acids are $SnCl_4$, $ZnCl_2$ and, in particular, $AlCl_3$ and $TiCl_4$.

The attachment of two aromatic rings can also be carried out by means of the Ullmann reaction (for example Synthesis 1974, 9) between aryl iodides using copper iodide, but preferably between an aryl-copper compound and an aryl iodide, or by the Gomber-Bachmann reaction between an aryldiazonium salt and the corresponding aromatic compound (for example Org. React. 2 224 (1944)). The preparation of the tolanes of the formula I ($Z=-C\equiv C-$) is effected, for example, by reacting the corresponding aryl halides with an acetylide in a basic solvent with transition metal catalysis; palladium catalysts can preferably be used here, in particular a mixture of bis-(triphenylphosphine)-palladium-(II) chloride and copper iodide in piperidine as solvent.

In addition, the compounds of the formula I can be prepared by reducing a compound which otherwise corresponds to the formula I but which contains one or more reducible groups and/or C—C bonds instead of H atoms.

Suitable reducible groups are preferably carbonyl groups, in particular keto groups, and also, for example, free or esterified hydroxyl groups or halogen atoms attached to aromatic nuclei. Preferred starting materials for the reduction are compounds which correspond to the formula I, but which contain a cyclohexene ring or cyclohexanone ring instead of a cyclohexane ring and-/or contain a $-CH=CH-$ group instead of a $-CH_2CH_2-$ group and/or contain a $-CO-$ group instead of a $-CH_2-$ group and/or contain a free or functionally modified (for example in the form of its p-toluenesulfonate) OH group instead of an H atom.

The reduction can, for example, be effected by catalyst hydrogenation at temperatures between about 0° and about 200° and pressures between about 1 and 200 bar, in an inert solvent, for example an alcohol, such as methanol, ethanol or isopropanol, an ether, such as tetrahydrofuran (THF) or dioxane, an ester, such as ethyl acetate, a carboxylic acid, such as acetic acid, or a hydrocarbon, such as cyclohexane. Suitable catalysts are preferably noble metals, such as Pt or Pd, which can be employed in the form of oxides (for example $PtO_2$ or PdO), on a support (for example Pd on charcoal, calcium carbonate or strontium carbonate) or in a finely divided form.

Ketones can also be reduced by the methods of Clemmensen (using zinc, amalgamated zinc or tin and hydrochloric acid, preferably in aqueous-alcoholic solution or in a heterogeneous phase containing water/toluene at temperatures between about 80° and 120°) or Wolff-Kishner (using hydrazine, preferably in the presence of an alkali, such as KOH or NaOH, in a high-boiling solvent, such as diethylene glycol or triethylene glycol at temperatures between about 100° and 200°) to give the corresponding compounds of the formula I containing alkyl groups and/or —$CH_2CH_2$— bridges.

Reductions by means of complex hydrides are also possible. For example, arylsulfonyloxy groups can be removed reductively by means of $LiAlH_4$, in particular particular p-toluenesulfonyloxymethyl groups can be reduced to methyl groups, preferably in an inert solvent, such as diethyl ether or THF, at temperatures between about 0° and 100°. Double bonds can be hydrogepated using $NaBH_4$ or tributyltin hydride in methanol.

Suitable diluents are preferably ethers, such as diethyl ether, dibutyl ether, tetrahydrofuran or dioxane, amides, such as dimethylformamide or hexamethylphosphoric acid triamide, hydrocarbons, such as hexane, cyclohexane, benzene, toluene or xylene, halogenated hydrocarbons, such as methylene dichloride, chloroform, carbon tetrachloride or tetrachloroethylene, sulfoxides, such as dimethyl sulfoxide or sulfolan, alcohols, such as methanol, ethanol or isopropanol, and other organic solvents, such as acetonitrile and nitromethane. Water or mixtures of these solvents with one another and/or with water are also suitable for the above reaction. The reaction temperatures are between −20° and +100°, preferably between 0° and 50°. At these temperatures the reactions are, as a rule, complete after 30 minutes to 24 hours.

The liquid-crystal phases according to the invention consist of 2 to 25, preferably 3 to 15, components, including at least one compound of the formula I. The other constituents are preferably selected from the nematic or nematogenic substances, especially the known substances, belonging to the classes of the azoxybenzenes, benzylideneanilines, biphenyls, terphenyls, phenyl or cyclohexyl benzoates, phenyl or cyclohexyl cyclohexanecarboxylates, phenylcyclohexanes, cyclohexylbiphenyls, cyclohexylcyclohexanes, cyclohexylnaphthalenes, 1,4-bis-cyclohexylbenzenes, 4,4'-bis-cyclohexylbiphenyls, phenylpyrimidines, cyclohexylpyrimidines, phenyldioxanes, cyclohexyldioxanes, phenyldithianes, cyclohexyldithianes, 1,2-bis-phenylethanes, 1,2-bis-cyclohexylethanes, 1-phenyl-2-cyclohexylethanes, optionally halogenated stilbenes, benzyl phenyl ethers, tolanes and substituted cinnamic acids.

The must important compounds which are suitable as constituents of liquid-crystal phases of this type can be characterized by means of the formula II

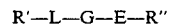

$$R'—L—G—E—R''\qquad\text{II}$$

wherein L and E are each a carbocyclic or heterocyclic ring system composed of the group formed from 1,4-disubstituted benzene and cyclohexane rings, 4,4'-disubstituted biphenylcyclohexane, phenylcyclohexane and cyclohexylcyclohexane systems, 2,5-disubstituted pyrimidine and 1,3-dioxane rings, 2,6-disubstituted naphthalene, di-hydronaphthalene, tetrahydronaphthalene, quinazoline and tetrahydroquinazoline,

| Gas is | |
|---|---|
| —CH=CH— | —N(O)=N— |
| —CH=CY— | —CH=N(O)— |
| —C≡C— | —$CH_2$—$CH_2$— |
| —CO—O— | —$CH_2$—O— |
| —CO—S— | —$CH_2$—S— |
| CH=CH=N— | —COO—Phe—COO— | or a C—C single bond, Y is halogen, preferably chlorine, or —CN, and R' and R'' are alkyl, alkoxy, alkanoyloxy or alkoxycarbonyloxy having up to 18, preferably up to 8, carbon atoms, or one of these radicals can also be CN, $NO_2$, $CF_3$, F, Cl or Br.

In most of these compounds R' and R'' are different from one another, one of these radicals being in most cases an alkyl or alkoxy group. Other variants of the substituents envisaged are also customary, however. Many substances of this type or mixtures thereof are commercially available. All these substances can be prepared by methods known from the literature.

The liquid-crystal phases according to the invention contain about 0.1 to 99%, preferably 10 to 95%, of one or more compounds of the formula I. Liquid-crystal phases . . . (sic) 0.1–40%, in particular 0.5–29%, of one or more compounds of the formula I are also preferred.

Dielectrics according to the invention containing 0.1 to 40%, preferably 0.5 to 30%, of one or more compounds of the formula I are also preferred.

Compounds of the formula I having an optically active wing group are suitable for use as components of nematic liquid-crystal phases in order to avoid reverse twist and to improve the elastic constants.

The optically active compounds of the formula I are also suitable for use as components of chirally tilted, smectic, liquid-crystal phases.

The preparation of the dielectrics according to the invention is effected in a manner customary per se. As a rule, the components are dissolved in one another, preferably at an elevated temperature.

By means of suitable additives it is possible to modify the liquid-crystal dielectrics according to the invention in such a way that they can be used in all hitherto disclosed types of liquid-crystals display elements.

Additives of this type are known to those skilled in the art and are described in detail in the literature. For example, it is possible to add conducting salts, preferably ethyldimethyldodecylammonium 4-hexyloxybenzoate, tetrabutylammonium tetraphenylboranate or complex salts of crown ethers (cf., for example, I. Haller et al., Mol.Cryst.Liq.Cryst. Volume 24, pages 249–258 (1973)) in order to improve the conductivity, to add dichroic dyestuffs in order to prepare colored guest-host systems or to add substances for altering the dielectric anisotropy, the viscosity and/or the orientation of the nematic phases. Substances of this type are described, for example, in German Offenlegungsschriften 2,209,127, 2,240,854, 2,321,632, 2,338,281, 2,450,088, 2,637,430, 2,853,728 and 2,902,177.

The following examples are intended to illustrate the invention without limiting it. m.p.=melting point; c.p.=clear point. In the preceding and following text percentages are percentages by weight; all temperature data are quoted in degrees centigrade. "Customary working up" means as follows: if necessary, water is added, the mixture is extracted with methylene chloride, ether or toluene, the phases are separated, the organic phase is dried and evaporated and the product is purified by distillation under reduced pressure cr crystallization and/or chromatography.

EXAMPLE 1

A mixture of 11.6 g of p-pentylbenzoyl chloride, 11.1 g of p-hydroxyphenyl sulfur pentafluoride and 100 ml of pyridine is stirred it room temperature for 20 hours. Concentrating the mixture and working it up in the customary manner gives 4-(4-pentylbenzoyloxy)-phenylsulfur pentafluoride.

The following are prepared analogously:
4-(4-ethylbenzoyloxy)-phenyl-sulfur pentafluoride
4-(4-propylbenzoyloxy)-phenyl-sulfur pentafluoride
4-(4-butylbenzoyloxy)-phenyl-sulfur pentafluoride
4-(4-hexylbenzoyloxy)-phenyl-sulfur pentafluoride
4-(4-heptylbenzoyloxy)-phenyl-sulfur pentafluoride
4-(4-octylbenzoyloxy)-phenyl-sulfur pentafluoride
4-(4-methoxybenzoyloxy)-phenyl-sulfur pentafluoride
4-(4-ethoxybenzoyloxy)-phenyl-sulfur pentafluoride
4-(4-propoxybenzoyloxy)-phenyl-sulfur pentafluoride
4-(4-butoxybenzoyloxy)-phenyl-sulfur pentafluoride
4-(4-hexyloxybenzoyloxy)-phenyl-sulfur pentafluoride
4-(4-heptyloxybenzoyloxy)-phenyl-sulfur pentafluoride
4-(4-octyloxybenzoyloxy)-phenyl-sulfur pentafluoride
4-(4-(trans-4-ethylcyclohexyl)benzoyloxy)-phenyl-sulfur pentafluoride
4-(4-(trans-4-propylcyclohexyl)benzoyloxy)-phenyl-sulfur pentafluoride
4-(4-(trans-4-butylcyclohexyl)benzoyloxy)-phenyl-sulfur pentafluoride
4-(4-(trans-4-hexylcyclohexyl)benzoyloxy)-phenyl-sulfur pentafluoride
4-(4-(trans-4-heptylcyclohexyl)benzoyloxy)-phenyl-sulfur pentafluoride
4-(4-(trans-4-octylcyclohexyl)benzoyloxy)-phenyl-sulfur pentafluoride
4-(4-(trans-4-methoxycyclohexyl)benzoyloxy)-phenyl-sulfur pentafluoride
4-(4-(trans-4-ethoxycyclohexyl)benzoyloxy)-phenyl-sulfur pentafluoride
4-(4-(trans-4-propoxycyclohexyl)benzoyloxy)-phenyl-sulfur pentafluoride
4-(4-(trans-4-butoxycyclohexyl)benzoyloxy)-phenyl-$ulfur pentafluoride
4-(4-(trans-4-pentoxycyclohexyl)benzoyloxy)-phenyl-sulfur pentafluoride
4-(4-(trans-4-hexoxycyclohexyl)benzoyloxy)-phenyl-sulfur pentafluoride
4-(4-(trans-4-heptyloxycyclohexyl)benzoyloxy)-phenylsulfur pentafluoride
4-(4-(trans-4-octyloxycyclohexyl)benzoyloxy)-phenyl-sulfur pentafluoride
4-(4-ethylbenzoyloxy)-2-fluorophenyl-sulfur pentafluoride
4-(4-propylbenzoyloxy)-2-fluorophenyl-sulfur pentafluoride
4-(4-butylbenzoyloxy)-2-fluorophenyl-sulfur pentafluoride
4-(4-pentylbenzoyloxy)-2-fluorophenyl-sulfur pentafluoride
4-(4-hexylbenzoyloxy)-2-fluorophenyl-sulfur pentafluoride
4-(4-heptylbenzoyloxy)-2-fluorophenyl-sulfur pentafluoride
4-(4-octylbenzoyloxy)-2-fluorophenyl-sulfur pentafluoride
4-(4-ethoxybenzoyloxy)-2-fluorophenyl-sulfur pentafluoride
4-(4-propoxybenzoyloxy)-2-fluorophenyl-sulfur pentaflouride
4-(4-butoxybenzoyloxy)-2-fluorophenyl-sulfur pentafluoride
4-(4-pentoxybenzoyloxy)-2-fluorophenyl-sulfur pentafluoride
4-(4-hexoxybenzoyloxy)-2-fluorophenyl-sulfur pentafluoride
4-(4-ethylbenzoyloxy)-2-chlorophenyl-sulfur pentafluoride
4-(4-propylbenzoyloxy)-2-chlorophenyl-sulfur pentafluoride
4-(4-butylbenzoyloxy)-2-chlorophenyl-sulfur pentafluoride
4-(4-pentylbenzoyloxy)-2-chlorophenyl-sulfur pentafluoride
4-(4-hexylbenzoyloxy)-2-chlorophenyl-sulfur pentafluoride
4-(4-heptylbenzoyloxy)-2-chlorophenyl-sulfur pentafluoride
4-(4-octylbenzoyloxy)-2-chlorophenyl-sulfur pentafluoride
4-(4-ethoxybenzoyloxy)-2-chlorophenyl-sulfur pentafluoride
4-(4-propoxybenzoyloxy)-2-chlorophenyl-sulfur pentafluoride
4-(4-butoxybenzoyloxy)-2-chlorophenyl-sulfur pentafluoride
4-(4-pentoxybenzoyloxy)-2-chlorcphenyl-sulfur pentafluoride
4-(4-hexoxybenzoyloxy)-2-chlorophenyl-sulfur pentafluoride
4-(4-heptyloxybenzoyloxy)-2-chlorophenyl-sulfur pentafluoride
4-(4-octyloxybenzoyloxy)-2-chlorophenyl-sulfur pentafluoride

EXAMPLE 2

A mixture of 10.6 g of dicyclohexylcarbodiimide and 40 ml of methylene chloride is added to a mixture of 9.1 g of trans-4-pentylcyclohexylcarboxylic acid, 11.2 g of p-hydroxyphenyl-sulfur pentafluoride and 100 ml of methylene chloride, and the combined mixture is heated at the boil for 6 hours. Working up in the customary manner gives 4-(trans-4-pentylcyclohexylcarbonyloxy)-phenyl-sulfur pentafluoride.

The following are prepared analogously:
4-(trans-4-ethylcyclohexylcarbonyloxy)-phenyl-sulfur pentafluoride
4-(trans-4-propylcyclohexylcarbonyloxy)-phenyl-sulfur pentafluoride
4-(trans-4-butylcyclohexylcarbonyloxy)-phenyl-sulfur pentafluoride 4-(trans-4-hexylcyclohexylcarbonyloxy)-phenyl-sulfur pentafluoride
4-(trans-4-heptylcyclohexylcarbonyloxy)-phenyl-sulfur pentafluoride
4-(trans-4-octylcyclohexylcarbonyloxy)-phenyl-sulfur pentafluoride
4-(trans-4-(trans-4-ethylcyclohexyl)-cyclohexylcarbonyl-oxy)-phenyl-sulfur pentafluoride
4-(trans-4-(trans-4-propylcyclohexyl)-cyclohexylcarbonyl-oxy)-phenyl-sulfur pentafluoride
4-(trans-4-(trans-4-butylcyclohexyl)-cyclohexylcarbonyl-oxy)-phenyl-sulfur pentafluoride
4-(trans-4-(trans-4-pentylcyclohexyl)-cyclohexylcarbonyl-oxy)-phenyl-sulfur pentafluoride
4-(trans-4-(trans-4-hexylcyclohexyl)-cyclohexylcarbonyl-oxy)-phenyl-sulfur pentafluoride
4-(trans-4-(trans-4-heptylcyclohexyl)-cyclohexylcarbonyl-oxy)-phenyl-sulfur pentafluoride
4-(trans-4-(trans-4-octylcyclohexyl)-cyclohhxylcarbonyl-oxy)-phenyl-sulfur pentafluoride
4-(trans-4-(4-ethylphenyl)-cyclohexylcarbonyloxy)-phenyl-sulfur pentafluoride
4-(trans-4-(4-propylphenyl)-cyclohexylcarbonyloxy)-phenyl-sulfur pentafluoride
4-(trans-4-(4-butylphenyl)-cyclohexylcarbonyloxy)-phenyl-sulfur pentafluoride
4-(trans-4-(4-pentylpheryl)-cyclohexylcarbonyloxy)-phenyl-sulfur pentafluoride
4-(trans-4-(4-hexylphenyl)-cyclohexylcarbonyloxy)-phenyl-sulfur pentafluoride
4-(trans-4-(4-heptylphenyl)-cyclohexylcarbonyloxy)-phenyl-sulfur pentafluoride
4-(trans-4-(4-octylphenyl)-cyclohexylcarbonyloxy)-phenyl-sulfur pentafluoride
4-(trans-4-ethylcyclohexylcarbonyloxy)-2-fluorophenyl-sulfur pentafluoride
4-(trans-4-propylcyclohexylcarbonyloxy)-2-fluorophenyl-sulfur pentafluoride
4-(trans-4-butylcyclohexylcarbonyloxy)-2-fluorophenyl-sulfur pentafluoride
4-(trans-4-hexylcyclohexylcarbonyloxy)-2-fluorophenyl-sulfur pentafluoride
4-(trans-4-heptylcyclohexylcarbonyloxy)-2-fluorophenyl-sulfur pentafluoride
4-(trans-4-ethylcyclohexylcarbonyloxy)-2-chlorophenyl-sulfur pentafluoride
4-(trans-4-propylcyclohexylcarbonyloxy)-2-chlorophenyl-sulfur pentafluoride
4-(trans-4-butylcyclohexylcarbonyloxy)-2-chlorophenyl-sulfur pentafluoride
4-(trans-4-hexylcyclohexylcarbonyloxy)-2-chlorophenyl-sulfur pentafluoride
4-(trans-4-heptylcyclohexylcarbonyloxy)-2-chlorophenyl-sulfur pentafluoride
4-(trans-4-(4-ethylphenyl)-cyclohexylcarbonyloxy)-2-fluoro sulfur pentafluoride (sic)
4-(trans-4-(4-propylphenyl)-cyclohexylcarbonyloxy)-2-fluoro sulfur pentafluoride (sic)
4-(trans-4-(4-butylphenyl)-cyclohexylcarbonyloxy)-2-fluoro sulfur pentafluoride (sic)
4-(trans-4-(4-pentylphenyl)-cyclohexylcarbonyloxy)-2-fluoro sulfur pentafluoride (sic)
4-(trans-4-(4-hexylphenyl)-cyclohexylcarbonyloxy)-2-fluoro sulfur pentafluoride (sic)
4-(trans-4-(4-hextylphenyl)-cyclohexylcarbonyloxy)-2-fluoro sulfur pentafluoride (sic)
4-(trans-4-(4-ethoxyphenyl)-cyclohexylcarbonyloxy)-2-fluoro sulfur pentafluoride (sic)
4-(trans-4-(4-propoxyphenyl)-cyclohexylcarbonyloxy)-2-fluoro sulfur pentafluoride (sic)
4-(trans-4-(4-butoxyphenyl)-cyclohexylcarbonyloxy)-2-fluoro sulfur pentafluoride (sic)
4-(trans-4-(4-pentoxyphenyl)-cyclohexylcarbonyloxy)-2-fluoro sulfur pentafluoride (sic)
4-(trans-4-(4-hexoxyphenyl)-cyclohexylcarbonyloxy)-2-fluoro sulfur pentafluoride (sic)
4-(trans-4-(4-heptoxylphenyl)-cyclohexylcarbonyloxy)-2-fluoro sulfur pentafluoride (sic)
4-(trans-4-(4-octyloxylphenyl)-cyclohexylcarbonyloxy)-2-fluoro sulfur pentafluoride (sic)

EXAMPLE 3

A mixture of 2.9 g of 4-propylcyclohexanone and 10 ml of tetrahydrofuran is added dropwise to a mixture of 4-bromomagnesiumphenyl-sulfur pentafluoride (prepared from 5.6 g of 4-bromophenyl-sulfur pentafluoride, 0.5 g of magnesium turnings and 0.05 g of iodine) and 20 ml of tetrahydrofuran. 40 ml of half-concentrated hydrochloric acid are added, the solid constituents are removed and the aqueous phase is separated off and concentrated, and the residue which remains is then dissolved in 40 ml of toluene, 5.0 g of p-toluenesulfonic acid are added and the mixture is heated at the boil for 3 hours. Working up in the customary manrer gives 4-(4-propylcyclohex-1-enyl)-phenyl-sulfur pentafluoride.

The following are prepared analogously:
4-(4-ethylcyclohex-1-enyl)-phenyl-sulfur pentafluoride
4-(4-butylcyclohex-1-enyl)-phenyl-sulfur pentafluoride
4-(4-pentylcyclohex-1-enyl)-phenyl-sulfur pentafluoride
4-(4-hexylcyclohex-1-enyl)-phenyl-sulfur pentafluoride
4-(4-heptylcyclohex-1-enyl)-phenyl-sulfur pentafluoride
4-(4-octylcyclohex-1-enyl)-phenyl-sulfur pentafluoride
4-(4-(4-ethylphenyl)-cyclohex-1-enyl)-phenyl-sulfur pentafluoride
4-(4-(4-propylphenyl)cyclohex-1-enyl)-phenyl-sulfur pentafluoride
4-(4-(4-butylphenyl)cyclohex-1-enyl)-phenyl-sulfur pentafluoride
4-(4-(4-pentylphenyl)-cyclohex-1-enyl)-phenyl-sulfur pentafluoride
4-(4-(4-hexylphenyl)-cyclohex-1-enyl)-phenyl-sulfur pentafluoride
4-(4-(4-heptylphenyl)-cyclohex-1-enyl)-phenyl-sulfur pentafluoride
4-(4-(4-octylphenyl)-cyclohex-1-enyl)-phenyl-sulfur pentafluoride
4-(4-(trans-4-ethylcyclohexyl)-cyclohex-1-enyl)-phenyl-sulfur pentafluoride
4-(4-(trans-4-propylcyclohexyl)-cyclohex-1-enyl)-phenyl-sulfur pentafluoride
4-(4-(trans-4-butylcyclohexyl)-cyclohex-1-enyl)-phenyl-sulfur pentafluoride
4-(4-(trans-4-pentylcyclohexyl)-cyclohex-1-enyl)-phenyl-sulfur pentafluoride
4-(4-(trans-4-hexylcyclohexy)-cyclohex-1-enyl)-phenyl-sulfur pentafluoride
4-(4-(trans-4-heptylcyclohexyl)-cyclohex-1-enyl)-phenyl-sulfur pentafluoride
4-(4-(trans-4-octylcyclohexyl)-cyclohex-1-enyl)-phenyl-sulfur pentafluoride

EXAMPLE 4

A mixture of 6.5 g of 4-(4-pentylcyclohex-1-enyl)-phenyl-sulfur pentafluoride, 0.5 g of palladium-on-active charcoal (1%) and 40 ml of toluene is hydrogenated at room temperature under normal pressure until saturation is reached. Removing the solvent by distillation and working up in the customary manner gives 4-(trans-4-pentylcyclohexyl)-phenyl-sulfur pentafluoride.

The following are prepared analogously:
4-(trans-4-ethylcyclohexyl)-phenyl-sulfur pentafluoride
4-(trans-4-butylcyclohexyl)-phenyl-sulfur pentafluoride
4-(trans-4-pentylcyclohexyl)-phenyl-sulfur pentafluoride
4-(trans-4-hexylcyclohexyl)-phenyl-sulfur pentafluoride
4-(trans-4-heptylcyclohexyl)-phenyl-sulfur pentafluoride
4-(trans-4-octylcyclohexyl)-phenyl-sulfur pentafluoride
4-(trans-4-(4-ethylphenyl)-cyclohexyl)-phenyl-sulfur pentafluoride
4-(trans-4-(4-propylphenyl)-cyclohexyl)-phenyl-sulfur pentafluoride
4-(trans-4-(4-butylphenyl)-cyclohexyl)-phenyl-sulfur pentafluoride
4-(trans-4-(4-hexylphenyl)-cyclohexyl)-phenyl-sulfur pentafluoride
4-(trans-4-(4-heptylphenyl)-cyclohexyl)-phenyl-sulfur pentafluoride
4-(trans-4-(4-octylphenyl)-cyclohexyl)-phenyl-sulfur pentafluoride
4-(trans-4-(trans-4-ethylcyclohexyl)-cyclohexyl)-phenyl-sulfur pentafluoride
4-(trans-4-(trans-4-propylcyclohexyl)-cyclohexyl)-phenyl-sulfur pentafluoride
4-(trans-4-(trans-4-butylcyclohexyl)-cyclohexyl)-phenyl-sulfur pentafluoride
4-(trans-4-(trans-4-hexylcyclohexyl)-cyclohexyl)-phenyl-sulfur pentafluoride
4-(trans-4-(trans-4-heptylcyclohexyl)-cyclohexyl)-phenyl-sulfur pentafluoride
4-(trans-4-(trans-4-octylcyclohexyl)-cyclohexyl)-phenyl-sulfur pentafluoride

EXAMPLE 5

A mixture of 18.3 g of 4-bromophenyl-sulfur pentafluoride and 50 ml of tetrahydrofuran is added to a mixture of the organozinc compound prepared from 28.7 g of 1-bromo-4-(trans-4-propylcyclohexyl)-cyclohexane and 7 g of zinc, 13 g of nickel(II) chloride and tetrahydrofuran, and the mixture is heated at the boil for 5 hours. Working up in the customary manner gives 4-(trans-4-(trans-4-propylcyclohexyl)-cyclohexyl)-phenyl-sulfur pentafluoride.

The following are prepared analogously:
4-(trans-4-(trans-4-ethylcyclohexyl)-cyclohexyl)-phenyl-sulfur pentafluoride
4-(trans-4-(trans-4-butylcyclohexyl)-cyclohexyl)-phenyl-sulfur pentafluoride
4-(trans-4-(trans-4-pentylcyclohexyl)-cyclohexyl)-phenyl-sulfur pentafluoride
4-(trans-4-(trans-4-hexylcyclohexyl)-cyclohexyl)-phenyl-sulfur pentafluoride
4-(trans-4-(trans-4-heptylcyclohexyl)-cyclohexyl)-phenyl-sulfur pentafluoride
4-(trans-4-(trans-4-octylcyclohexyl)-cyclohexyl)-phenyl- C sulfur pentafluoride
4-(4-ethylbicyclo[2.2.2]octyl)-phenyl-sulfur pentafluoride
4-(4-propylbicyclo[2.2.2]octyl)-phenyl-sulfur pentafluoride
4-(4-butylbicyclo[2.2.2]octyl)-phenyl-sulfur pentafluoride
4-(4-pentylbicyclo[2.2.2]octyl)-phenyl-sulfur pentafluoride fluoride
4-(4-heptylbicyclo[2.2.2]octyl)-phenyl-sulfur pentafluoride
4-(4-octylbicyclo[2.2.2]octyl)-phenyl-sulfur pentafluoride
4-(4-ethoxybicyclo[2.2.2]octyl)-phenyl-sulfur pentafluoride
4-(4-propoxybicyclo[2.2.2]octyl)-phenyl-sulfur pentafluoride
4-(4-butoxybicyclo[2.2.2]octyl)-phenyl-sulfur pentafluoride
4-(4-pentoxybicyclo[2.2.2]octyl)-phenyl-sulfur pentafluoride
4-(4-hexoxybicyclo[2.2.2]octyl)-phenyl-sulfur pentafluoride
4-(4-heptyloxybicyclo[2.2.2]octyl)-phenyl-sulfur pentafluoride
4-(4-octyloxybicyclo[2.2.2]octyl)-phenyl-sulfur pentafluoride

EXAMPLE 6

A mixture of 6.0 g of trans-1-iodomethyl-4-propylcyclohexane and 10 ml of dimethylformamide is added to a mixture of 4.4 g of 4-hydroxyphenyl-sulfur pentafluoride, 3.5 g of potassium carbonate and 20 ml of dimethylformamide, and the combined mixture is stirred at 100° C. for 2 hours. After solid constituents have been removed, working up in the customary manner gives 4-(4-trans-propylcyclohexylmethoxy)-phenyl-sulfur pentafluoride.

The following are prepared analogously:
4-(trans-4-ethylcyclohexylmethoxy)-phenyl-sulfur pentafluoride
4-(trans-4-butylcyclohexylmethoxy)-phenyl-sulfur pentafluoride
4-(trans-4-pentylcyclohexylmethoxy)-phenyl-sulfur pentafluoride
4-(trans-4-hexylcyclohexylmethoxy)-phenyl-sulfur pentafluoride
4-(trans-4-heptylcyclohexylmethoxy)-phenyl-sulfur pentafluoride
4-(trans-4-octylcyclohexylmethoxy)-phenyl-sulfur pentafluoride
4-(4-ethylbicyclo[2.2.2]octylmethoxy)-phenyl-sulfur pentafluoride
4-(4-propylbicyclo[2.2.2]octylmethoxy)-phenyl-sulfur pentafluoride
4-(4-butylbicyclo[2.2.2]octylmethoxy)-phenyl-sulfur pentafluoride
4-(4-pentylbicyclo[2.2.2]octylmethoxy)-phenyl-sulfur pentafluoride
4-(4-hexylbicyclo[2.2.2]octylmethoxy)-phenyl-sulfur pentafluoride
4-(4-heptylbicyclo[2.2.2]octylmethoxy)-phenyl-sulfur pentafluoride
4-(4-octylbicyclo[2.2.2]octylmethoxy)-phenyl-sulfur pentafluoride
4-(4-ethylbenzyloxy)-phenyl-sulfur pentafluoride
4-(4-propylbenzyloxy)-phenyl-sulfur pentafluoride
4-(4-butylbenzyloxy)-phenyl-sulfur pentafluoride
4-(4-pentylbenzyloxy)-phenyl-sulfur pentafluoride 4-(4-hexylbenzyloxy)-phenyl-sulfur pentafluoride
4-(4-heptylbenzyloxy)-phenyl-sulfur pentafluoride
4-(4-octylbenzyloxy)-phenyl-sulfur pentafluoride
4-(4-ethoxybenzyloxy)-phenyl-sulfur pentafluoride
4-(4-propoxybenzyloxy)-phenyl-sulfur pentafluoride
4-(4-butoxybenzyloxy)-phenyl-sulfur pentafluoride
4-(4-pentyloxybenzyloxy)-phenyl-sulfur pentafluoride
4-(4-hexoxybenzyloxy)-phenyl-sulfur pentafluoride
4-(4-heptyloxybenzyloxy)-phenyl-sulfur pentafluoride
4-(4-octyloxybenzyloxy)-phenyl-sulfur pentafluoride
4-(4-(trans-4-ethylcyclohexyl)-benzyloxy)-phenyl-sulfur pentafluoride
4-(4-(trans-4-propylcyclohexyl)-benzyloxy)-phenyl-sulfur pentafluoride
4-(4-(trans-4-butylcyclohexyl)benzyloxy)-phenyl-sulfur pentafluoride
4-(4-(trans-4-pentylcyclohexyl)-benzyloxy)-phenyl-sulfur pentafluoride
4-(4-(trans-4-hexylcyclohexyl)-benzyloxy)-phenyl-sulfur pentafluoride
4-(4-(trans-4-heptylcyclohexyl)-benzyloxy)-phenyl-sulfur pentafluoride
4-(4-(trans-4-octylcyclohexyl)-benzyloxy)-phenyl-sulfur pentafluoride

EXAMPLE 7

8.5 g of p-bromophenyl-sulfur pentafluoride and 20 ml of piperidine are added to a mixture of 8.5 g of 4-pentoxyphenylacetylene, 20 ml of piperidine, 420 mg of triphenylphosphine-palladium(II) chloride and 30 mg of copper iodide, and the combined mixture is heated for 20 hours. Concentration and working up in the customary manner gives 4-(2-(4-pentoxyphenyl)-ethynyl)-phenyl-sulfur pentafluoride.

The following are prepared analogously:
4-(2-(4-ethoxyphenyl)-ethynyl)-phenyl-sulfur pentafluoride
4-(2-(4-propoxyphenyl)-ethynyl)-phenyl-sulfur pentafluoride
4-(2-(4-butoxyphenyl)-ethynyl)-phenyl-sulfur pentafluoride
4-(2-(4-hexoxyphenyl)-ethynyl)-phenyl-sulfur pentafluoride
4-(2-(4-heptyloxyphenyl)-ethynyl)-phenyl-sulfur pentafluoride
4-(2-(4-octyloxyphenyl)-ethynyl)-phenyl-$ulfur pentafluoride
4-(2-(4-ethylphenyl)-ethynyl)-phenyl-sulfur pentafluoride
4-(2-(4-propylphenyl)-ethynyl)-phenyl-sulfur pentafluoride
4-(2-(4-butylphenyl)-ethynyl)-phenyl-sulfur pentafluoride
4-(2-(4-pentylphenyl)-ethynyl)-phenyl-sulfur pentafluoride
4-(2-(4-hexylphenyl)-ethynyl)-phenyl-sulfur pentafluoride
4-(2-(4-heptylphenyl)-ethynyl)-phenyl-sulfur pentafluoride
4-(2-(4-octylphenyl)-ethynyl)-phenyl-sulfur pentafluoride
4-(2-(trans-4-ethylcyclohexyl)-ethynyl)-phenyl-sulfur pentafluoride
4-(2-(trans-4-propylcyclohexyl)-ethynyl)-phenyl-sulfur pentafluoride
4-(2-(trans-4-butylcyclohexyl)-ethynyl)-phenyl-sulfur pentafluoride
4-(2-(trans-4-pentylcyclohexyl)-ethynyl)-phenyl-sulfur pentafluoride
4-(2-(trans-4-hexylcyclohexyl)-ethynyl)-phenyl-sulfur pentafluoride
4-(2-(trans-4-heptylcyclohexyl)-ethynyl)-phenyl-sulfur pentafluoride
4-(2-(trans-4-octylcyclohexyl)-ethynyl)-phenyl-sulfur pentafluoride
4-(2-(trans-4-ethoxycyclohexyl)-ethynyl)-phenyl-sulfur pentafluoride
4-(2-(trans-4-propoxycyclohexyl)-ethynyl)-phenyl-sulfur pentafluoride
4-(2-(trans-4-butoxycyclohexyl)-ethynyl)-phenyl-sulfur pentafluoride
4-(2-(trans-4-hexoxycyclohexyl)-ethynyl)-phenyl-sulfur pentafluoride
4-(2-(trans-4-heptyloxycyclohexyl)-ethynyl)-phenyl-sulfur pentafluoride
4-(2-(trans-4-octyloxycyclohexyl)-ethynyl)-phenyl-sulfur pentafluoride

EXAMPLE 8

A mixture of 11.4 g of 4-(2-(4-trans-pentylcyclohexyl)-ethynyl)-phenyl sulfur pentafluoride (prepared as in EXAMPLE 7), 50 ml of toLuene and 10 mg of palladium-on-active charcoal is hydrogenated at room temperature under normal pressure. The solid constituents are filtered off and the filtrate is concentrated and worked up in the customary manner to give 4-(2-(trans-4-pentylcyclohexyl)-ethyl)-phenyl-sulfur pentafluoride.

The following are prepared analogously:
4-(2-(trans-4-ethylcyclohexyl)-ethyl)-phenyl-sulfur pentafluoride
4-(2-(trans-4-propylcyclohexyl)-ethyl)-phenyl-sulfur pentafluoride
4-(2-(trans-4-butylcyclohexyl)-ethyl)-phenyl-sulfur pentafluoride
4-(2-(trans-4-hexylylcyclohexyl)-ethyl)-phenyl-sulfur pentafluoride
4-(2-(trans-4-heptylcyclohexyl)-ethyl)-phenyl-sulfur pentafluoride
4-(2-(trans-4-octylcyclohexyl)-ethyl)-phenyl-sulfur pentafluoride
4-(2-(trans-4-ethoxycyclohexyl)-ethyl)-phenyl-sulfur pentafluoride
4-(2-(trans-4-propoxycyclohexyl)-ethyl)-phenyl-sulfur pentafluoride
4-(2-(trans-4-butoxycyclohexyl)-ethyl)-phenyl-sulfur pentafluoride
4-(2-(trans-4-hexyloxycyclohexyl)-ethyl)-phenyl-sulfur pentafluoride
4-(2-(trans-4-heptyloxycyclohexyl)-ethyl)-phenyl-sulfur pentafluoride
4-(2-(trans-4-octyloxycyclohexyl)-ethyl)-phenyl-sulfur pentafluoride
4-(2-(4-ethylphenyl)-ethyl)-phenyl-sulfur pentafluoride
4-(2-(4-propylphenyl)-ethyl)-phenyl-sulfur pentafluoride
4-(2-(4-butylphenyl)-ethyl)-phenyl-sulfur pentafluoride
4-(2-(4-pentylphenyl)-ethyl)-phenyl-sulfur pentafluoride
4-(2-(4-hexylylphenyl)-ethyl)-phenyl-sulfur pentafluoride
4-(2-(4-heptylphenyl)-ethyl)-phenyl-sulfur pentafluoride
4-(2-(4-octylphenyl)-ethyl)-phenyl-sulfur pentafluoride
4-(2-(4-ethoxyphenyl)-ethyl)-phenyl-sulfur pentafluoride 4-(2-(4-propoxyphenyl)-ethyl)-phenyl-sulfur pentafluoride 4-(2-(4-butoxyphenyl)-ethyl)-phenyl-sulfur pentafluoride 4-(2-(4-pentoxyphenyl)-ethyl)-phenyl-sulfur pentafluoride 4-(2-(4-hexyloxyphenyl)-ethyl)-phenyl-sulfur pentafluoride 4-(2-(4-heptyloxyphenyl)-ethyl)-phenyl-sulfur pentafluoride 4-(2-(4-octyloxyphenyl)-ethyl)-phenyl-sulfur pentafluoride

EXAMPLE A

A liquid-crystal mixture is prepared, having the following composition:

10% of p-cyanophenyl p-ethylbenzoate,
11% of p-cyanophenyl p-butylbenzoate,
9% of p-ethoxyphenyl trans-4-propylcyclohexanecarboxylate,
24% of p-butoxyphenyl trans-4-propylcyclohexanecarboxylate,
19% of p-ethoxyphenyl trans-4-butylcyclohexanecarboxylate,
21% of p-methoxyphenyl trans-4-pentylcyclohexanecarboxylate and
6% of 4-(4-pentylbenzoyloxy)-phenyl-sulfur pentafluoride.

We claim:

1. Aryl-sulfur pentafluorides of the formula I wherein

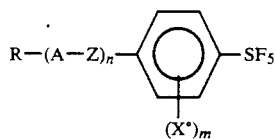

I

R is H, Y or an alkyl or alkenyl radical each of which has 1-15 C atoms and is unsubstituted or substituted by at least one group Y and in which one or more non-adjacent $CH_2$ groups can also be replaced by O and/or S atoms and/or by —E—, —CO—, —O—CO—, —CO—O—, —O—CO—O—, —S—CO— and/or —CO—S— groups, E is C≡C,

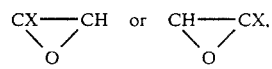

the $X^o$s independently of one another are each Y or $CH_3$, the Xs independently of one another are each $X^o$ or H, Y is CN, $N_3$, NCO, NCS, fluorine or chlorine, the As independently of one another are each a) a 1,4-cyclohexylene radical, wherein one or two non-adjacent $CH_2$ groups can be replaced by O atoms, b) a 1,4-phenylene radical, wherein one or more CH groups can be replaced by N, or c) a radical belonging to the group comprising 1,4-cyclohexenylene, piperidine-1,4-diyl, bicyclo-(2.2.2)octylene, naphthalene-2,6-diyl, decahydro-naphthalene-2,6-diyl or 1,2,3,4-tetrahydronaphthalene, it being possible for the radicals a) and b) to be monosubstituted or disubstituted by $X^o$, the Zs independently of one another are each —CO—O—, —O—CO—, —$CH_2CH_2$—, —$CHCN$—$CH_2$—, —$CH_2$—$CHCN$—, —CH=CH—, —C≡C—, —$OCH_2$—, —$CH_2O$—, —CH=N—, —N=CH—, —NO=N—, —N=NO— or a single bond, m is 0, 1 or 2 and n is 1, 2 or 3.

2. Liquid-crystal phase having at least two components, characterized in that it contains at least one compound of the formula I.

3. Liquid-crystal display element characterized in that it contains a liquid-crystal phase according to claim 2.

4. Electrooptical display element characterized in that it contains a phase according to claim 2 as the dielectric.

* * * * *